US00PP18659P3

(12) United States Plant Patent
Fear et al.

(10) Patent No.: US PP18,659 P3
(45) Date of Patent: Mar. 25, 2008

(54) RASPBERRY PLANT NAME 'DRISCOLL SEVILLANA'

(50) Latin Name: ***Rubus idaeus* L.**
Varietal Denomination: Driscoll Sevillana

(75) Inventors: Carlos Fear, Aptos, CA (US); Rick Harrison, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 128 days.

(21) Appl. No.: 11/327,110

(22) Filed: Jan. 6, 2006

(65) Prior Publication Data

US 2007/0163015 P1 Jul. 12, 2007

(51) Int. Cl.
*A01H 5/00* (2006.01)

(52) U.S. Cl. ..... Plt./204

(58) Field of Classification Search ..... Plt./204
See application file for complete search history.

*Primary Examiner*—Wendy C. Haas
*Assistant Examiner*—Georgia Helmer
(74) *Attorney, Agent, or Firm*—Jones Day

(57) ABSTRACT

The present invention relates to a new and distinct cultivar of raspberry plant named 'Driscoll Sevillana'. The new cultivar is distinguished from other raspberry cultivars by its large firm fruit with consistent fruit structure and high yield. The new cultivar is distinguished from its parent by being a less vigorous plant, producing more uniform and more elongated shape fruit, and having larger and less acidic fruit.

3 Drawing Sheets

1. Latin name of the genus and species of the plant claimed: The variety is botanically identified as *Rubus idaeus* L. subgenus *Rubus*.

1.2 Variety denomination: The Raspberry variety denomination is 'Driscoll Sevillana'.

2. BACKGROUND OF THE INVENTION

This invention relates to a new cultivar of raspberry called 'Driscoll Sevillana'. The new cultivar was developed from a single seedling selected from the hybridization of the selection 'Isabel' (U.S. Plant Pat. No. 9,340) as the seed parent with the selection 'Driscoll Cardinal' (U.S. Plant Pat. No. 14,903) as the pollen parent. The parents were crossed in 1998, whereafter fruit and seed were collected to produce seedlings for field planting in Oxnard, Calif. in 1999. The new cultivar was selected from these seedlings in 1999 for its large firm fruit. The new cultivar has been asexually propagated by in vitro shoot tip culture, root sucker division and root cuttings at the Cassin Ranch in Santa Cruz County, Calif. and has been shown to maintain the desired and distinguishing characteristics after propagation over several generations.

3. SUMMARY OF THE INVENTION

The present invention provides a new and distinct cultivar of red raspberry plant named 'Driscoll Sevillana'. The variety is botanically identified as *Rubus idaeus* L. The 'Driscoll Sevillana' red raspberry plant produces a primocane crop which begins in mid July and continues until early November. The floricane crop begins in late April and continues until late June. Both the primocane and floricane yields are high relative to other comparable varieties. The fruit of 'Driscoll Sevillana' is notably quite firm and very consistent with regard to its size and shape throughout its harvest period. The fruit of 'Driscoll Sevillana' separates easily from its receptacle.

4. BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics. The specimens in FIGS. 1–3 are about 11 months old.

5. DETAILED BOTANICAL DESCRIPTION

Figure 1:
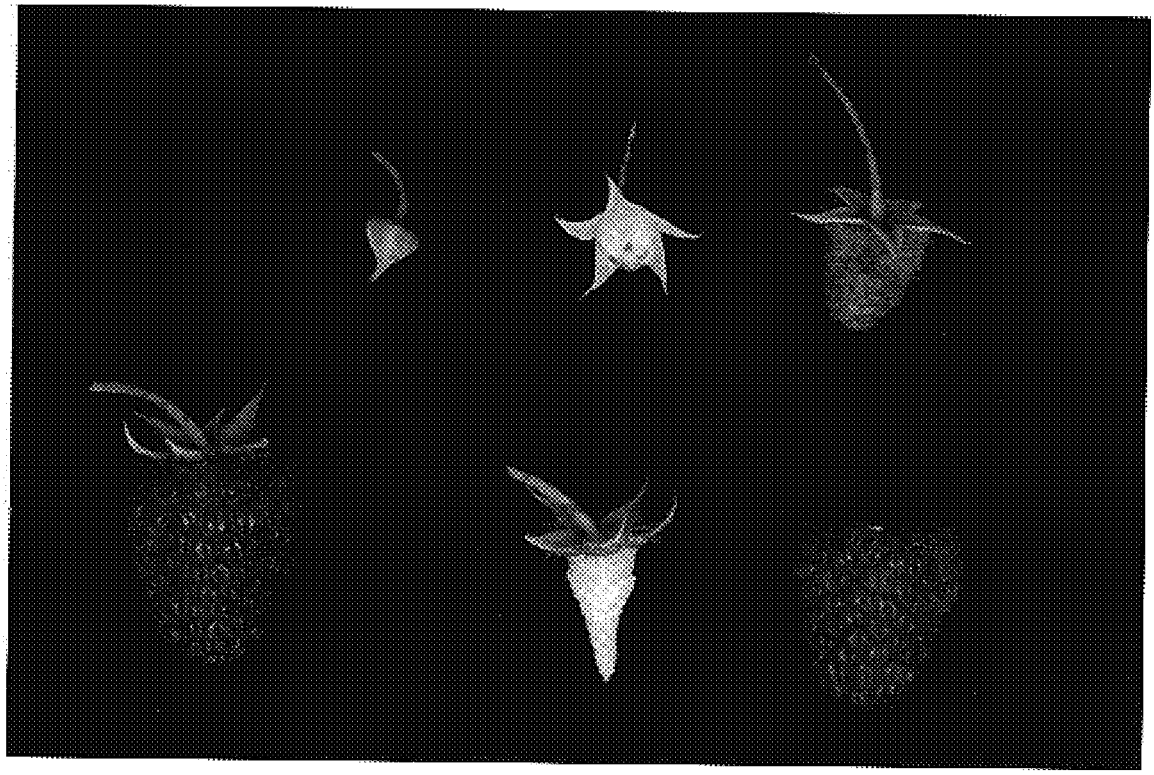
FIG. 1 is a photograph of 'Driscoll Sevillana' primocane flowers and fruit in various stages of development.
Figure 2:
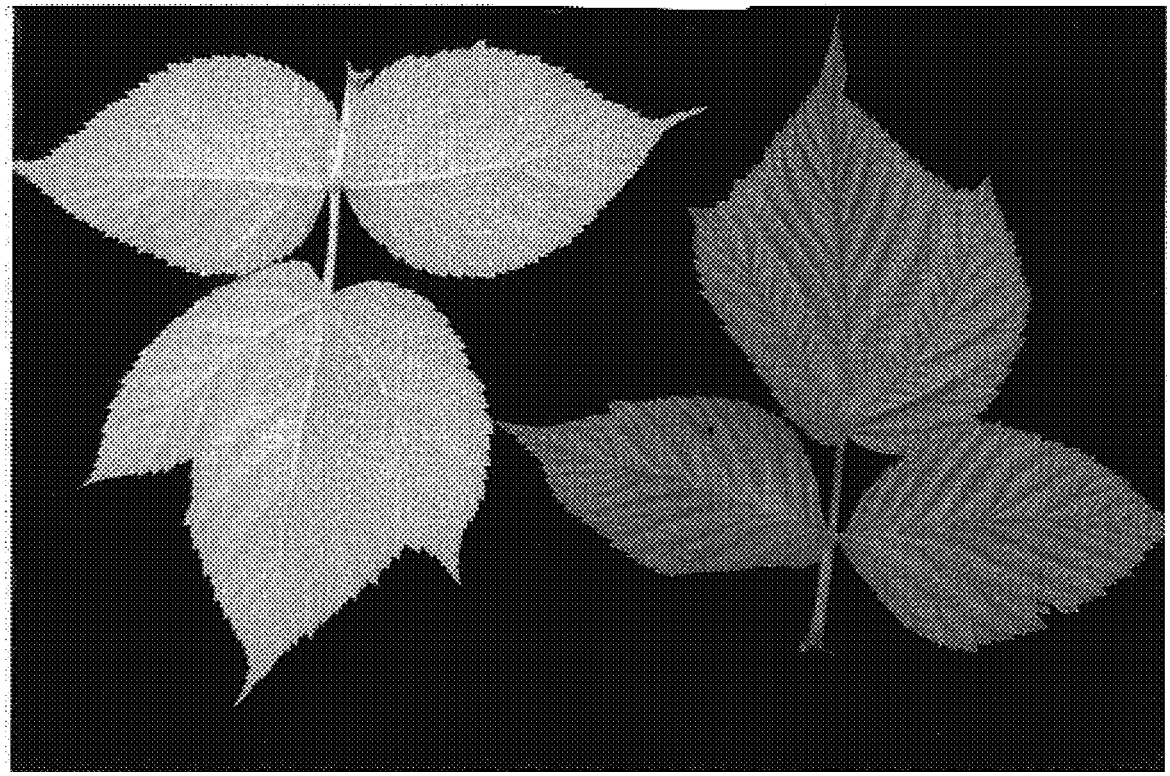
FIG. 2 is a photograph of 'Driscoll Sevillana' primocane leaves showing upper and lower leaf surfaces.
Figure 3:
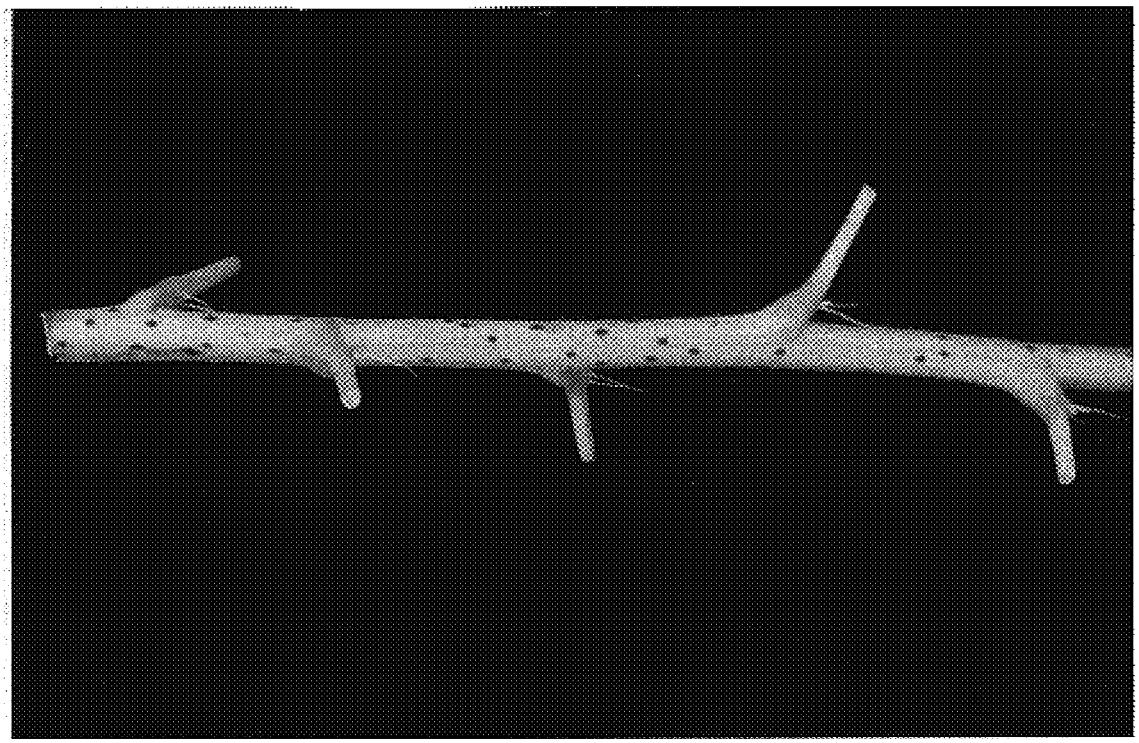
FIG. 3 is a photograph of a 'Driscoll Sevillana' primocane shoot.

The following detailed description of the new raspberry cultivar, 'Driscoll Sevillana', is based upon recorded observations of plants and fruit grown in Watsonville, Calif. between 2001 and 2002, and is believed to apply to plants of the 'Driscoll Sevillana' cultivar grown in similar conditions of soil and climate elsewhere.

Throughout this specification, color names beginning with a small letter signify that the name of the color, as used in common speech, is aptly descriptive. Color data beginning with a capital letter and followed by an alphanumeric code indicates the most similar color designations as provided by The Royal Horticultural Society (R.H.S.) Colour Chart published by the Royal Horticultural Society of London, England. Color designations, color descriptions, and other phenotypical descriptions may deviate from the stated values and descriptions depending upon variation in environmental, seasonal, climatic and cultural conditions.

Table 1 provides information on the plant and fruit characteristics of the new cultivar 'Driscoll Sevillana' compared with characteristics of the unpatented raspberry cultivar 'Heritage'. Comparisons of the cultivars were taken under similar conditions.

The new variety is particularly characterized and distinguished from other cultivars by its large firm fruit with consistent fruit structure and high yield. The fruit color of 'Driscoll Sevillana' is a medium red at harvest but darkens after harvest to a deeper color. Fruit of 'Driscoll Sevillana' separates easily from the receptacle and is of excellent firmness at harvest. The fruit of 'Driscoll Sevillana' is very consistent in size and shape throughout the harvest period.

The primocane and floricane yields of 'Driscoll Sevillana' are high relative to the variety 'Heritage'. 'Driscoll Sevillana' is distinguishable from its pollen parent, selection 'Isabel', by being a less vigorous plant and producing more uniform and more elongated shape fruit. The new cultivar is distinguished from its seed parent, selection 'Driscoll Cardinal', by having larger and less acidic fruit. Additional characteristics of 'Driscoll Sevillana' include an average flower diameter of about 8.2 mm.

5.1 DISEASE AND STRESS RESISTANCE

Resistance is unknown to powdery mildew and root rots. Cold tolerance of the new cultivar has not been established. Post harvest fruit rot resistance is good in comparison over many selections and varieties.

TABLE 1

PLANT CHARACTERISTICS OF 'DRISCOLL SEVILLANA'

| | Driscoll Sevillana | Heritage |
|---|---|---|
| GENERAL | | |
| Plant Size | Small-Med | Large |
| Growth habit | Erect | Erect |
| Productivity | High | Medium |
| Self-fruitfulness | Self-fruitful | Self-fruitful |
| Time of bud burst | Early | Late |
| Primocane fruiting | | |
| Percent of cane Length flowering as Primocane | 40-60 | 20-40 |
| Percent of total yield | 60 | 53 |
| Primocanes | | |
| Number of young shoots | Many | Medium |
| Young shoot pigmentation | Medium | Medium |
| Length (cm) | 123 | 195 |
| Time of shoot emergence | Early | Medium |
| Glaucosity (waxy bloom) | Weak | Weak |
| Strength | Medium | Medium |
| Cane cross section (from mid cane of primocane) | Angular | Rounded to angular |
| Dormant cane color | 166-A | 166-B |
| Prickles | | |
| Pigmentation | Brown to purple | Green-brownish to green |
| Density on young shoots | Medium | Dense |
| Attitude of tip | Downward | Downward |
| Size | Medium | Medium |
| Size: Length (mm) (base to tip at 1 m height at end of harvest) | 1.7 | 2 |

TABLE 1-continued

PLANT CHARACTERISTICS OF 'DRISCOLL SEVILLANA'

| | Driscoll Sevillana | Heritage |
|---|---|---|
| Texture | Heavy | Heavy |
| Presence and distribution of petioles | Present, regularly distributed | Present, regularly distributed |
| Pubescence on canes | Absent | Absent |
| Internodal distance (cm) (at central 1/3 of cane) | 4.1 | 4.3 |
| LEAVES | | |
| Color | | |
| Face | 147-A | 147-A |
| Underside | 148-C | 148-C |
| Relief between veins | Weak | Weak |
| Glossiness | Medium | Medium |
| Petiole | | |
| Length (cm) | 4.4 | 7.0 |
| Pigmentation of upper surface | Absent | Lightly |
| Pigmentation of underside | Unpigmented | Unpigmented |
| Stipule orientation | Erect | Erect |
| Arrangement | Compound | Compound |
| Number of leaflets | Sometimes 3, Sometimes 5 | Sometimes 3, sometimes 5 |
| Overlapping of lateral leaflets | Free to touching | Free to touching |
| Lateral leaflet: length to stalklet (lower pair) | Very short | Very short |
| Terminal leaflet | | |
| Length (cm) | 11.5 | 14.8 |
| Width (cm) | 9.5 | 8.8 |
| Shape | Ovate | Ovate |
| Tip | Acuminate | Acuminate |
| Base | Cordate | Rounded |
| Margin | Doubly serrate | Doubly serrate |
| Lateral leaflets (basal pair) | | |
| Length (cm) | 10.1 | 13.7 |
| Width | 6.6 | 7.8 |
| Orientation | Opposite | Opposite |
| Shape | Ovate | Ovate |
| Tip | Acuminate | Acuminate |
| Base | Oblique | Oblique |
| Margin | Doubly serrate | Doubly serrate |
| Rachis length between terminal leaflet and adjacent lateral leaflet (cm) | 2.5-4.5 | 3.7-5.8 |
| FLOWERS | | |
| Flowering period | | |
| Primocane | Mid June through Early October | Early July through Early October |
| Floricane | Late March through Late May | Mid April through Mid June |
| Flower size | Medium | Medium |
| Petal | | |
| Length (cm) | 0.8 | 0.7 |
| Width (cm) | 0.3 | 0.3 |
| Pedicel | | |
| Coloration | Present | Present, strong Intensity |
| Length | Medium | Short to medium |
| FRUIT | | |
| Harvest Season | | |
| Primocane | Mid July-early November | Early August-early November |
| Floricane | Late April-late June | Late May-mid July |

TABLE 1-continued

PLANT CHARACTERISTICS OF 'DRISCOLL SEVILLANA'

| | Driscoll Sevillana | Heritage |
|---|---|---|
| Color | Medium Red | Medium Red |
| Immature | 180-A | 180-A |
| Maturing | 182-A | 185-B |
| Mature fruit | 185-A | 185-A |
| Glossiness | Medium | Medium |
| Shape | Ovate | Ovate |
| Dimensions | | |
| Size | Medium | Small |
| Length (mm) | 21 | 19 |
| Width (mm) | 21 | 19 |
| Length:width | 1.0 | 1.0 |
| Weight (g/Fruit) | | |
| Primocane | 4.8 | 3.4 |
| Floricane | 4.1 | 2.6 |
| Soluble Solids (%) | 9.0 | 10.5 |

TABLE 1-continued

PLANT CHARACTERISTICS OF 'DRISCOLL SEVILLANA'

| | Driscoll Sevillana | Heritage |
|---|---|---|
| Titratable acidity (% as citric acid) | 1.80 | 1.50 |
| Seeds | | |
| Weight (mg) | 1.74 | 1.62 |
| Number druplets/fruit | 81 | 75 |
| Adherence to plug (1-9) | Medium | Medium |
| Firmness | Medium to firm | Firm |
| Yield | High | Medium |

What is claimed:

1. A new and distinctive cultivar of raspberry plant, substantially as shown and described.

* * * * *